United States Patent [19]
Siqueira

[11] Patent Number: 5,939,461
[45] Date of Patent: Aug. 17, 1999

[54] DISINFECTING COMPOSITION

[75] Inventor: Vera Lucia Siqueira, Sao Paulo, Brazil

[73] Assignee: Lever Brothers Company, New York, N.Y.

[21] Appl. No.: 08/979,732

[22] Filed: Aug. 15, 1995

[30] Foreign Application Priority Data

Aug. 16, 1994 [GB] United Kingdom .................... 9416478

[51] Int. Cl.⁶ ..................................................... A01N 33/12
[52] U.S. Cl. ........................................... 514/642; 514/643
[58] Field of Search ..................................... 514/642, 643; 424/196.1

[56] References Cited

U.S. PATENT DOCUMENTS 4,336,151  6/1982  Like et al. ................................ 510/106

FOREIGN PATENT DOCUMENTS 1120820  3/1982  Canada .

*Primary Examiner*—Jose' G. Dees
*Attorney, Agent, or Firm*—Neil Y. Gilbert

[57] ABSTRACT

The present invention provides a disinfecting composition which comprises: 1–5% of a quaternary nitrogen antibacterial agent preferably an alkyl aryl dimethyl ammonium salt of a monovalent anion, 0.5–5% of a terpenoid containing oil, preferably a pine oil and 0.1–3% of a nonionic surfactant selected from the group comprising:
a) ethoxylated alcohols with an alkyl chain length of at least 16 carbons and an ethoxylation value of at least 21, preferably a C18–C20 ethoxylated alcohol with an ethoxylation value of 21–60 and,
b) ethoxy/propoxy copolymers of molecular weight in excess of 4000.

2 Claims, No Drawings

DISINFECTING COMPOSITION

TECHNICAL FIELD

The present invention relates to a disinfecting composition.

BACKGROUND OF THE INVENTION

Disinfecting compositions which comprise nonionic surfactants and quaternary bacteriocides are known. Other known formulations comprise anionic actives and antibacterial agents such as Irgasan DP300 (TM) and formaldehyde. Still further compositions are based on phenols and terpines.

Some groups of consumers require a disinfecting composition to give a visible indication of it's presence in dilute solution. In the past this has been accomplished by the use of water-insoluble terpenoid materials which have been solubilised by the presence of a surfactant. Upon dilution these compositions become cloudy or milky.

BRIEF DESCRIPTION OF THE INVENTION

We have now determined that particular ethoxylated alcohols and alkoxylate polymers enable a similar 'milky' effect to be achieved in dilute formulations Accordingly, the present invention provides a disinfecting composition which comprises:

a) 1–5% of a quaternary nitrogen antibacterial agent,
b) 0.1–3% of a nonionic surfactant selected from the group comprising:
  1) ethoxylated alcohols with an alkyl chain length of at least 16 carbons and an ethoxylation value of at least 21, and,
  2) ethoxy/propoxy copolymers of molecular weight in excess of 4000,
c) 0.5–5% of a terpenoid containing oil.

DETAILED DESCRIPTION OF THE INVENTION

In preferred embodiments of the invention, the quaternary nitrogen antibacterial agent is a alkyl aryl dimethyl ammonium salt of a monovalent anion, or a corresponding salt in which one or both of the methyl groups has been replaced by a C2–C4 alkyl chain. Typically the first above-mentioned alkyl chain has a length of C8–C22. Preferably the antibacterial agent is an alkyl benzyl dimethyl ammonium halide, preferably the chloride.

Typical levels of the quaternary nitrogen antibacterial agent range from 2–3% wt of the composition.

The preferred nonionic surfactants include C16–C24, preferably C18–C20 ethoxylated alcohols with an ethoxylation value of 21–60. Suitable materials include Ultroil RH 250 (TM) a C18–25EO alcohol ethoxylate and Ultradel R540 (TM) a C18–50EO alcohol ethoxylate. A particular advantage of these ethoxylated alcohols is that the composition is not sensitive to hard-water unlike soap based systems.

The preferred nonionic surfactants also include the ethoxy/propoxy copolymers of molecular weight of 4000–20000. More preferably the materials have a ratio of ethoxy to propoxy groups which favours the propoxylate. Suitable materials include Genapol PF20 (TM) an 20% ethoxy/80% propoxy block co-polymer.

Typical levels of the nonionic range from 0.5–1.5% wt of the composition.

The preferred terpenoid containing oils include pine oils and other terpenoid containing oils derived from plants, although the use of synthetic oils is not intended to be excluded.

The preferred levels of the terpenoid containing oil range from 1–35 wt of the composition.

Compositions according to the present invention can further comprise optional components including perfumes, at typical levels of 0.1–1% wt and colouring agents at levels of 0.0001–0.01% wt. Preferably, the compositions are free of soaps, any soap present being at a level of less than 2% wt on the composition.

Particularly preferred compositions comprise:

a) 2–3% of a C8–C18 aryl dimethyl ammonium halide,
b) 0.25–1.5% of a nonionic surfactant selected from the group comprising:
  1) ethoxylated alcohols with an alkyl chain length of at least 18–20 carbons and an ethoxylation value of 21–60, and,
  2) ethoxy/propoxy copolymers, having an excess of propoxy residues, said copolymers being of molecular weight in the range 4000–20000,
c) 1–3% of a terpenoid containing plant oil.

In order that the present invention may be further understood it will be illustrated hereafter by reference to examples.

EXAMPLES

Samples were prepared with the compositions of examples 1–5 as given in Table 1 below. The materials are identified as follows:

QUAT: alkyl dimethyl benzyl ammonium chloride,
NON1: GENAPOL PF20, 20EO/80PO copolymer,
NON2: ULTRIOL RH 250 C18–25EO alcohol ethoxylate,
NON3: ULTRADEL R540 C18–50EO alcohol ethoxylate,
NON4: UNITOL C12–6EO alcohol ethoxylate,
NON5: C18–20EO alcohol ethoxylate,
PINE: Pine oil,
COLR: Commercially available colour/pigment
PERF: Commercially available perfume.

TABLE 1

| COMPONENTS | EXAMPLE 1 | 2 | 3 | 4 | 5 |
|---|---|---|---|---|---|
| QUAT | 2.5 | 2.5 | 2.5 | 2.5 | 2.5 |
| NON1 | 0.8 | — | — | — | — |
| NON2 | — | 0.8 | — | — | — |
| NON3 | — | — | 0.8 | — | — |
| NON4 | — | — | — | 0.8 | — |
| NON5 | — | — | — | — | 0.8 |
| PINE | 2.0 | 2.0 | 2.0 | 2.0 | 2.0 |
| PERF | 0.5 | 0.5 | 0.5 | 0.5 | 0.5 |
| COLR | tr | tr | tr | tr | tr |
| Water | --------to 100% wt-------- | | | | |
| milky | yes | yes | yes | yes | yes |

The score given at 'milky' indicates whether the composition turned milky when diluted with an excess of water. From the results it can be seen that the effect was noted with the higher molecular weight materials but not with the two lower molecular weight materials of examples 4 and 5.

I claim:

1. A disinfecting composition which comprises:

a) 1–5% by weight of a quateary nitrogen antibacterial agent,
b) 0.1–3% by weight of a nonionic surfactant selected from the group comprising:
  1) ethoxylated alcohols with an alkyl chain length of at least 16 carbons and an ethoxylation value of at least 21, and, 2) ethoxy/propoxy opolymers of molecular weight in excess of 4000, and, c) 0.5–5% by weight of a terpenoid containing oil.

2. Composition according to claim 1 comprising, a) 2–3% by weight of a C8–C18 aryl dimethyl ammonium halide, b) 0.25–1.5% by weight of a nonionic surfactant selected from the group comprising:

1) ethoxylated alcohols with an alkyl chain length of at least 18–20 carbons and an ethoxylation value of 21–60, and, 2) ethoxy/propoxy copolymers, having an excess of propoxy residues, said copolymers being of molecular weight in the range 4,000 to 20,000, and, 3) 1–3% by weight of a terpenoid containing plant oil.

* * * * *